United States Patent [19]

Stark

[11] 4,456,691

[45] Jun. 26, 1984

[54] ANTIGEN FOR PCB, ANTIBODY RAISED BY SAME, AND METHOD OF MAKING SAME

[76] Inventor: Suad Stark, 395 Riverside Dr., New York, N.Y. 10025

[21] Appl. No.: 470,497

[22] Filed: Feb. 28, 1983

[51] Int. Cl.³ .................... A61K 39/00; C07G 7/00
[52] U.S. Cl. ......................... 436/543; 260/112 B; 424/85; 436/547; 436/815; 436/822
[58] Field of Search ................. 436/543–547; 260/112 B; 424/85

[56] References Cited

U.S. PATENT DOCUMENTS

| | | | |
|---|---|---|---|
| 3,976,763 | 8/1976 | Spector | 424/85 |
| 3,995,021 | 11/1976 | Gross | 424/85 |
| 4,036,823 | 7/1977 | Soares | 260/112 R |
| 4,196,185 | 4/1980 | Focella et al. | 260/112 B |
| 4,238,472 | 12/1980 | Albro et al. | 436/543 |
| 4,342,826 | 8/1982 | Cole | 435/7 |

OTHER PUBLICATIONS

Becker et al., J. Tox. Enivrion. Health, vol. 9 (1982): 225–234.
Luster et al., Tox. Appl. Pharmacol., vol. 50 (1979): 147–155.
Byrne et al., Bull. Environm. Contam. Tox., vol. 26 (1981) 237–242.
Fed. Am. Biological. Societies, Abstract #7648 (Mar. 1982).
Newsome et al., Chem. Abstracts, vol. 96 (1982) #120982a.
Nose, Chem. Abstracts, vol. 79 (1973) #101573f.
Kohli et al., Chem. Abstracts, vol. 91 (1979) #84409.

*Primary Examiner*—Christine M. Nucker
*Attorney, Agent, or Firm*—James & Franklin

[57] ABSTRACT

A polychlorinated biphenyl hapten is covalently bonded to a macromolecule carrier through a diazo-containing linking group. In forming the conjugate, a PCB hapten is nitrated, aminated, diazotized and finally coupled with the macromolecule carrier. The antigen may be used to raise antibodies specific to the hapten and binding with the hapten.

12 Claims, No Drawings

ANTIGEN FOR PCB, ANTIBODY RAISED BY SAME, AND METHOD OF MAKING SAME

BACKGROUND OF THE INVENTION

The present invention relates to antigens and, more particularly, to a synthetic antigen for polychlorinated biphenyls, a method of making same, and an antibody raised by the same.

Polychlorinated biphenyls (PCB) comprise a large group of chemically very stable compounds. They are heat stable, non-volatile and non-biodegradable. Due to these physical properties PCB has been extensively utilized since the 1980's as insulating materials, thermal conductors in electrical equipment, hydraulic oils, and plasticizers in rubber and synthetic resins. PCB has also been used for dust control, as components of newspaper and carbonless copy paper ink, for moisture proofing components of foodpacking materials, for sealing and impregnation, as vapor suppressants and incorporated into insecticides (such as DDT and Dieldrin) to prolong kill life and increase toxicity.

PCB was not produced on a large scale until about 1929. The synthesis of PCB by catalytic chlorination of biphenyl produces a complex mixture of different homologs and isomers. Theoretically 209 different PCB isomers may exist, and available data indicate that approximately 80–90 are present in commercial PCB mixtures. Marine environments or human tissue may contain up to 40-50 PCB isomers. The Monsanto Company, the principal producer of PCB within the United States, markets these compounds under the trade name of Aroclor. The Aroclor mixtures are designated by four digit numbers, the last two digits of which generally define the percentage of chlorine by weight. Thus Aroclor 1254 is a mixture of polychlorinated biphenyl isomers with a total of 54% chlorine. The isomeric composition of Aroclor 1254 is 11% tetrachloro-, 49% pentachloro-, 34% hexachloro-, and 6% heptachlorbipheyl.

PCB is distributed in oceans, fresh water and estuaries. It has mutagenic effects on animals, fish and birds. It is generally taxic in animals and may produce a variety of symptoms including chlorance, porphyria, hematologic alterations, thymic atrophy and lymphatic changes as well as adverse effects on the liver and kidney tissue, gastric mucosa, and menstrual and reproductive cycles. It has a relatively long half-life of about 25 years. In view of the toxicity of PCB and its long half-life, on the one hand, and the complexity of its analytical analysis in aqueous media, on the other, a rapid method for quantifying it is of utmost importance.

Radioimmunoassay (RIA) is a specific, sensitive, precise and economical technique for microdetermination of compounds in aqueous systems. The prior art techniques for assessing compounds, including gas chromotography and mass spectrophotometry, have certain disadvantages not encountered by RIA. On the other hand, RIA requires an antibody. The essence of the immune system is its ability to recognize surface features of macromolecules that are not normal constituents of the organism. Antibodies are protein molecules produced by organism that carry out this specific recognition. The foreign entities that they recognize are called antigens. The portion of the antigen to which an antibody binds is called an antigenic determinant. An immunogen is an antigen that elicits a response from the immune system. Macromolecules such as foreign proteins, nucleic acids, and carbohydrates usually are effective immunogens. Molecules with molecular weights of less than 5000 usually are not. However, low molecular weight compounds not antigenic by themselves (termed haptens) can act as a potent antigenic determinants, if they form a covalent bond with a large carrier macromolecule to form a conjugate. The low molecular weight substance must contain at least one functional group capable of covalently bonding to an available functional group of the carrier. Characteristically strong covalent bonds are required to prevent in vivo lysis or cleavage of the conjugate during the immunization process. Furthermore, neither structural alteration of the low molecular weight substance nor denaturation of the carrier can occur during conjugation if a useful antigen is to be produced. The conjugate must also remain soluble to preserve reactivity.

Accordingly, it is an object of the present invention to provide a synthetic antigen for PCB.

Another object is to provide an antibody raised by such an antigen.

A further object is to provide a method of synthesizing such an antigen.

SUMMARY OF THE INVENTION

It has now been found that the above and related objects of the present invention are obtained in a synthetic antigen comprising at least one polychlorinated biphenylhapten bonded covalently through an azo-containing linking group to a macromolecule carrier which confers antigenicity.

In a preferred embodiment the carrier is bovine serum albumen and contains a tyrosine residue by means of which the carrier is linked to the azo-containing linking group. The hapten is preferably a mixture of various polychlorinated biphenyls, and the azo-containing linking group preferably consists of an azo group.

The antigen preferably has the formula

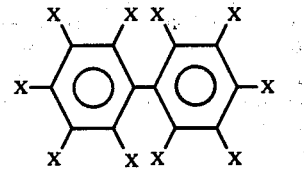

where X is selected from the class consisting of hydrogen, chlorine or —N=N— carrier, at least two of said X being chlorine and at least one of said X being —N=N— carrier.

The antigen is prepared by the steps of nitrating a polychlorinated biphenyl hapten; aminating the nitrated hapten; diazotizing the aminated hapten; and covalently coupling the diazotized hapten with a macromolecule carrier which confers antigenicity.

The hapten is preferably nitrated by reaction with nitric acid, aminated by reaction with glacial acetic acid and zinc powder, and diazotized by reaction with hydrochloric acid and sodium nitrate. The nitrated hapten is preferably purified by recrystallization with hot ethanol, the aminated hapten by recrystallization with hot ether and hot ethanol, and the coupled hapten by differential precipitation with ammonium sulfate dialysis and lyophilization. During the coupling step the pH of the reaction mixture is maintained at 9.4 plus or minus 0.5.

The present invention further comprises the antibody raised by the antigen and binding with the hapten. Preferably the antibody is specific to polychlorinated biphenyls and prepared by innoculating a host animal with the antigen and collecting the serum from the host animal.

DETAILED DESCRIPTION OF THE PREFERRED EMBODIMENTS

PCB Arochlor 1254 is nitrated, for example, with 90% fuming nitric acid. Nitration can be done also with sulfuric acid ($H_2SO_4$) and nonfuming nitric acid ($HNO_3$), or a mixture thereof called "mixed acid". Since sulfuric acid can complicate the mechanistic picture, 90% fuming nitric acid is preferably used. The 90% fuming nitric acid is preferably used in large excess to minimize complications due to water formed in the reaction. The product is purified by recrystallization several times in hot 95% ethanol until a constant melting point is achieved.

The nitrated PCB is then aminated, for example, with glacial acetic acid and zinc powder at 4° C. Other acids (both weak and strong) and other metals (such as Cu, Sn, Ni, Pt, etc.) and other temperatures may be used. The nitrated PCB can also be aminated by catalytic hydrogenation using molecular hydrogen. In a weakly acidic solution of the type used, the free amine is easily liberated by the addition of base and can be steam distilled off from the reaction mixture. The remaining crude aminated PCB is contaminated. It is soluble in aqueous mineral acid, however, while the nitro compound is not; thus it can be separated from the nitro compound with petroleum ether, for example. The separated amine compound is purified with hot petroleum ether and then recrystallized several times with 95% hot ethanol until a constant melting point is achieved.

The aminated PCB is then diazotized, preferably by adding a mineral acid and a few drops of sodium nitrite. Nitrous acid, an unstable compound, is produced in the presence of the amine by the reaction between sodium nitrite (0.1% $NaNO_2$) and a mineral acid, usually hydrochloric acid (0.1N HCl) or sulfuric acid. Hydrochloric acid is the preferred mineral acid. To prevent side reactions, excess mineral acid is used (more than two equivalents per mole PCB amine).

Prior to diazotization the mixture of the aminated PCB and the mineral acid is cooled in an ice bath to a temperature between 0° C. and 10° C. An aqueous solution of the sodium nitrite is then added at such a rate that the temperature does not rise above 5°-10° C. Since there is some loss of nitrous acid as NO and $NO_2$, it is necessary to test the reaction mixture to see when enough sodium nitrite has been added. This may be done with starch-iodide paper. (If there is excess nitrous acid, urea can be added). The solution of diazotized PCB is preferably used immediately after preparation since diazonium salts slowly decompose even at ice-bath temperatures.

The diazotized PCB is then coupled with a carrier macromolecule such as BSA in mildly alkaline solution, e.g., a borate buffer solution adjusted with sodium hydroxide. It is important that the coupling medium be adjusted to the right degree of alkalinity, within a pH range of 8.9-9.9, preferably 9.3-9.7, optimally 9.4.

The carrier macromolecule can be a natural or synthetic substance. For example, it can be a protein, a glyco-protein, a nucleoprotein, a polypeptide, a polysaccharide, a lipopolysaccharide, or a polyaminoacid. The preferred natural carrier macromolecule is the protein such as bovine serum albumin (BSA), human immunogammaglobulin (HGG), thyroglobulin, etc..

The advantage of using bovine serum albumin (BSA) as the carrier in this system is its availability, low cost, excellent immunogenicity, high degree of solubility and relative resistance to denaturation under the rigorous chemical conditions of the conjugation procedure. BSA is likely to yield a soluble conjugate which has been demonstrated by the fact that steroid-protein are soluble above pH 5.5. There are 21 tyrosine residues in BSA conjugated to BSA available for diazotization. To achieve a molecule with an outer periphery of haptens, several haptens are conjugated to a single carrier macromolecule. The coupling reaction takes place between a tyrosine residue and the diazonium salt of the PCB, with a coupling efficiency of approximately 30%.

The antigen or conjugate is then put through several purification steps which include differential precipitation with ammonium sulfate, dialysis and lyophilization. Column chromotography may also be used in the purification steps.

Thus, the essential steps used in preparing the PCB antigens involve nitration, amination, diazotization and coupling to a macromolecule carrier as in the following general formula:

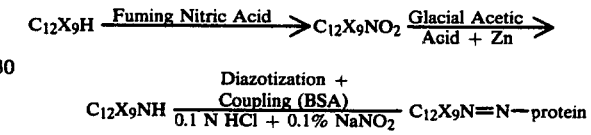

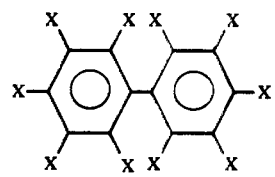

The antigen has the general formula where X is selected from the class consisting of hydrogen, chlorine, or —N=N— carrier, at least 2 of said X being chlorine and at least 1 of said X being —N=N— carrier.

An antigen of the present invention may be administered to vertebrate animals (such as rabbits, goats, horses, etc.) to raise antibodies. The resulting antibody will have multiple active sites that can selectively complex with polychlorinated biphenyl isomers similar to those in the hapten.

The specific antibodies of the present invention are useful reagents in biochemical assays for the determination of PCB in aqueous media. A preferred assay in the radioimmunoassay which includes isotopically labelled PCB with [$^{14}$C], [$^{3}$H], or [$^{125}$I]. It is possible to determine as little as 100 pg of PCB in aqueous media in 10 microliters.

EXAMPLES

EXAMPLE I

Nitration of PCB Aroclor 1254

10 grams of PCB Aroclor 1254 (obtained from Monsanto, St. Louis, Mo.) were slowly added over about 30 minutes with rapid stirring to 60 grams of fuming nitric acid cooled to 0° C. in an ice bath. After all the PCB Aroclor 1254 was added, stirring was continued for two and a half hours, with the temperature being maintained at 0° C. The mixture was then poured into cracked ice made from distilled water. This mixture was then filtered through a Buchner funnel. The precipitate was purified by several recrystallizations from hot 95% ethanol and dried with nitrogen. A melting point was obtained after each crystallization. The final constant melting point was 178°–181° C.

EXAMPLE II

Amination of the Nitrated PCB Aroclor 1254

5 grams of water and 5 grams of granulated zinc powder were added to 27 mgs of glacial acetic acid and 123 mgs of nitrated PCB Aroclor 1254 from Example I, and mixed with constant stirring. The resulting mixture was then incubated in a 38° C. water bath for fifteen minutes, diluted with water and filtered. The amine filtrate, separated from any remaining zinc, was extracted from nitro compounds with hot petroleum ether. The amine precipitate was purified to white crystals by several recrystallizations with hot 95% ethanol until a constant melting point of 152°–154° C. was achieved.

EXAMPLE III (a) Diazotization of PCB Aroclor 1254 Amine 0.627 mg of aminated PCB Aroclor 1254 from Example II was diazotized by slowly adding to it 12 mls of 0.1N HCl, and then very slowly adding 5 drops of 0.1% $NaNO_2$ with constant stirring throughout. The temperature was maintained at 4° C. for fifteen minutes. The $NaNO_2$ addition was carefully controlled by testing the mixture with starch iodide paper to avoid excess $HNO_2$.

(b) Coupling of Diazotized PCB Aroclor 1254 Amine to BSA

The coupling reaction was performed throughout at 4° C. 0.5 gram of BSA was dissolved in 5 ml borate buffer with the solution being maintained at pH 9.5 with 0.1N NaOH. 62.7 mg of diazotized PCB Aroclor 1254 of Example III(a) was added slowly. The pH of the mixture was maintained at 9.3–9.7, and the solution was mixed for two hours. The mixture was allowed to stand in a refrigerator overnight. The resulting compound was isolated and purified by differential precipitation with ammonium sulfate, dialysis (4 changes of 2 liters phosphate buffered saline of pH 7.4), all at 4° C. The product was lyophilized over 48 hours.

PCB Aroclor 1254 conjugation to the BSA was determined by 2,4,6 trinitrobenzene sulfonic acid (TNBS) and the absorbance of a serial dilution was read at 337 mμ to estimate the number of free unconjugated lysines in the product. (Habeeb, A.Anal. Biochem. 14:328–336, 1966).

EXAMPLE IV

Production of Antibody

Four New Zealand white rabbits were injected intradermally with 0.5 mg of lyophilized BSA-PCB Aroclor 1254 conjugate from Example III(b) in 0.5 ml of 0.9% sterile saline and with 0.5 ml of Freund's complete adjuvant at 10 day intervals for 30 days and thereafter monthly for 16 months. After 120 days from the first injection, antibody titers were preformed on animal blood collected 10–14 days after each injection. The preferred rabbit produced antibody with 50% binding of 2,2′,4,4′,5,5′[$^{14}C$]hexachlorobiphenyl at a dilution of about $10^{-5}$.

To determine the antibody titer of the antiserum, 0.5 ml. of various dilutions of the antiserum was incubated for one hour with 0.5 ml. of [$^{14}C$]hexachlorobiphenyl at 10,000 CPM per 0.5 ml in assay tubes. For the dilutions sterile 0.9% saline was used. The antibody bound PCB was then separated from free PCB with dextran coated charcoal (DCC), using 0.4 ml of DCC added to each assay tube. (The DCC consisted of 0.625 gram Norit A charcoal (Scientific Products, Edison, N.J.) which has been prewashed to remove the fines and 1.875 grams of Dextran T-70 in 500 ml of sterile 0.9% saline and 0.1% bovine gamma globulin). After the DCC was added, each tube was vortexed and incubated for exactly 15 minutes during which time they were vortexed once again. The assay tubes were centrifuged for 20 minutes in a refrigerated centrifuge at 5000×g. 0.5 ml of the supernatant that contain antibody with [$^{14}C$] PCB and bound non-radioactive PCB were pipetted into 5 ml Nalgene plastic bags (Sybron/Nalge, Rochester, N.Y.) with 3 ml. of Hydrofluor (National Diagnostics, Somerville, N.J.). A Packard Tricarb Liquid Scintillation Counter #2425 (Packard Instruments, Hollis, N.Y.) was used to determine the B emission of each aliquot. The result of the titer was the antibody with 50% binding of 2,2′,4,4′,5,5′[$^{14}C$]hexachlorobiphenyl at a dilution of $10^{-5}$. The entire titer procedure was performed at 4° C.

The antibodies are suitable for use in radioimmunoassay procedure based on competitive binding.

Obviously while the use of PCB Aroclor 1254 hapten produces antibodies which are specific to the four component isomers thereof, should antibodies specific to fewer, greater or simply different PCB isomers be desired, these antibodies may be obtained simply by using an appropriately different PCB isomer or mixture as the starting point hapten.

To summarize, the present invention provides a synthetic antigen for PCB, an antibody raised by such an antigen, and a method of synthesizing such an antigen. The PCB hapten is coupled to the macromolecule carrier by a covalent bond to confer immunogenicity to the conjugate.

Now that the preferred embodiments of the present invention have been described, various modifications and improvements thereon will become readily apparent to those skilled in the art. Accordingly, the spirit and scope of the present invention is to be limited only by the appended claims, and not by the foregoing disclosure.

I claim:

1. A synthetic antigen comprising at least one polychlorinated biphenyl hapten bonded covalently through an azo-containing linking group to a macromolecule carrier which confers antigenicity.

2. The antigen of claim 1 wherein said carrier is bovine serum albumin.

3. The antigen of claim 1 wherein said azo-containing linking group consists of an azo group.

4. The antigen of claim 1 wherein said antigen has the formula

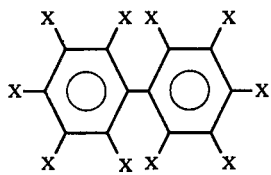

where X is selected from the class consisting of hydrogen, chlorine, or —N=N— carrier, at least 2 of said X being chlorine and at least 1 of said X being —N=N— carrier.

5. The antigen of claim 1 wherein said hapten is a mixture of various polychlorinated biphenyls.

6. The antigen of claim 1 wherein said carrier contains a tyrosine residue and is linked to said azo-containing linking group through said residue.

7. An antibody raised by said antigen of claim 1 and binding with said hapten.

8. The antibody of claim 7 specific to polychlorinated biphenyls prepared by innoculating a host animal with said antigen and collecting the serum from the host animal.

9. A method of preparing an antigen comprising the following steps:
  (A) nitrating a polychlorinated biphenyl hapten;
  (B) aminating the nitrated hapten;
  (C) diazotizing the aminated hapten; and
  (D) covalently coupling the diazotized hapten with a macromolecule carrier which confers antigenicity.

10. The method of claim 9 wherein during said coupling step the pH of the reaction mixture is maintained at $9.4 \pm 0.5$.

11. The method of claim 9 wherein said hapten is nitrated in step (A) by reaction with nitric acid, aminated by in step (B) by reaction with glacial acetic acid and zinc powder, and diazotized in step (C) by reaction with hydrochloric acid and sodium nitrite.

12. The method of claim 11 wherein said nitrated hapten is purified by recrystallization with hot ethanol, said aminated hapten is purified by recrystallization with hot ether and hot ethanol, and said coupled hapten is purified by differential precipitation with ammonium sulfate dialysis and lyophilization.

* * * * *